US009739760B2

(12) United States Patent
Noda et al.

(10) Patent No.: US 9,739,760 B2
(45) Date of Patent: Aug. 22, 2017

(54) GAS SENSOR

(71) Applicant: DENSO CORPORATION, Kariya, Aichi-pref. (JP)

(72) Inventors: Hirofumi Noda, Kariya (JP); Hirokazu Yamada, Nagoya (JP); Satoshi Hino, Kariya (JP)

(73) Assignee: DENSO CORPORATION, Kariya (JP)

( * ) Notice: Subject to any disclaimer, the term of this patent is extended or adjusted under 35 U.S.C. 154(b) by 309 days.

(21) Appl. No.: 13/886,931

(22) Filed: May 3, 2013

(65) Prior Publication Data
US 2013/0305811 A1    Nov. 21, 2013

(30) Foreign Application Priority Data

May 17, 2012   (JP) .................................. 2012-113131
Jan. 11, 2013   (JP) .................................. 2013-003655

(51) Int. Cl.
*G01N 33/00* (2006.01)
*G01N 27/406* (2006.01)
*G01N 27/407* (2006.01)

(52) U.S. Cl.
CPC ..... *G01N 33/0027* (2013.01); *G01N 27/4062* (2013.01); *G01N 27/4075* (2013.01)

(58) Field of Classification Search
CPC ............. G01N 27/421; G01N 27/4078; G01N 33/0027; G01N 27/4062; G01N 27/4075;
(Continued)

(56) References Cited

U.S. PATENT DOCUMENTS 5,573,650 A  * 11/1996  Fukaya ................ G01N 27/407
                                                        204/400
6,068,746 A  *  5/2000  Kojima ................ G01N 27/407
                                                        204/421
(Continued)

FOREIGN PATENT DOCUMENTS

JP       10-132779       5/1998
JP     2003/043004       2/2003
(Continued)

OTHER PUBLICATIONS

Office Action (2 pgs.) dated May 7, 2014 issued in corresponding Japanese Application No. 2013-003655 with an at least partial English-language translation thereof (2 pgs.).

*Primary Examiner* — Randy Gibson
*Assistant Examiner* — Gedeon M Kidanu
(74) *Attorney, Agent, or Firm* — Nixon & Vanderhye P.C.

(57) ABSTRACT

The gas sensor includes a sensor element, a first insulator inside which the sensor element is inserted, a second insulator disposed on a proximal side of the first insulator so as to cover a proximal side of the sensor element, and a contact member held by the second insulator and sandwiching the sensor element. A proximal end portion of the first insulator and a distal end portion of the second insulator abut on each other in an axial direction. Each the proximal end portion and the distal end portion is provided with a positioning structure. The positioning structure is configured to restrict a relative movement between the first and second insulators in a sandwiching direction in which the sensor element is sandwiched by the contact member and in an orthogonal direction perpendicular to the sandwiching direction and in the axial direction.

6 Claims, 6 Drawing Sheets

(58) Field of Classification Search
CPC .. G01N 27/417; G01N 27/4077; B60R 22/16; Y10T 29/49117; C01B 3/065; C01B 2203/066; C01D 15/02; H01M 8/065; H01M 8/0656; H01M 2008/1095; Y02E 60/50; Y02E 60/362; Y02E 60/364
USPC ........................................ 73/23, 31; 204/424
See application file for complete search history.

(56) References Cited

U.S. PATENT DOCUMENTS

| | | | | |
|---|---|---|---|---|
| 6,708,551 | B2* | 3/2004 | Kojima | G01N 27/4077 |
| | | | | 204/424 |
| 7,178,382 | B2* | 2/2007 | Noda | G01N 27/4078 |
| | | | | 73/23.2 |
| 7,472,578 | B2* | 1/2009 | Yamauchi | G01N 27/407 |
| | | | | 204/424 |
| 7,497,109 | B2* | 3/2009 | Satou | G01N 27/4077 |
| | | | | 73/31.05 |
| 2001/0045120 | A1* | 11/2001 | Friese | G01N 27/4077 |
| | | | | 73/23.31 |
| 2003/0024300 | A1* | 2/2003 | Kojima | 73/31.05 |
| 2005/0126261 | A1* | 6/2005 | Matsuda | G01N 27/407 |
| | | | | 73/31.05 |
| 2005/0138989 | A1* | 6/2005 | Noda | G01N 27/4078 |
| | | | | 73/31.05 |
| 2006/0213254 | A1* | 9/2006 | Satou | G01N 27/4077 |
| | | | | 73/31.05 |
| 2007/0175267 | A1* | 8/2007 | Yamauchi | G01N 27/407 |
| | | | | 73/31.05 |
| 2008/0314117 | A1 | 12/2008 | Sato et al. | |
| 2013/0305811 | A1* | 11/2013 | Noda | G01N 33/0027 |
| | | | | 73/31.05 |

FOREIGN PATENT DOCUMENTS

| | | |
|---|---|---|
| JP | 2005-207907 | 8/2005 |
| JP | 2009/002846 | 1/2009 |
| JP | 2011-247641 | 12/2011 |

* cited by examiner

GAS SENSOR

This application claims priority to Japanese Patent Applications No. 2012-113131 filed on May 17, 2012 and No. 2013-3655 filed on Jan. 11, 2013, the entire contents of which are hereby incorporated by reference.

BACKGROUND OF THE INVENTION

1. Field of the Invention

The present invention relates to a gas sensor for detecting a concentration of a specific gas contained in a measurement gas.

2. Description of Related Art

There are known various gas sensors which can be mounted on an exhaust system of an internal engine of a vehicle for measuring a concentration of a specific gas such as oxygen or nitrogen oxide contained in an exhaust gas as a measurement gas. Such gas sensors includes ones that include a sensor element for detecting a concentration of a specific gas contained in a measurement gas, a first insulator through which the sensor element is inserted to be held therein, a second insulator disposed on the proximal side of the first insulator so as to cover the proximal side of the sensor element, and a contact member held by the second insulator and being in contact with electrode terminals of the sensor element. For example, refer to Japanese Patent Application Laid-open No. 2003-43004.

The gas sensor described in this patent document includes a positioning structure provided in the end surface on the distal side of each of the first and second insulators for positioning the first and second insulators. The positioning structure of this gas sensor is configured to restrict movements of the first and second insulators in the direction perpendicular to the direction in which the sensor element is resiliently restrained or held by an electrode spring serving as the contact member. Restricting movements of the first and second insulators makes it possible to fix the positional relationship between the sensor element and the electrode spring in this direction to thereby provide a reliable electrical continuity between them.

However, in the gas sensor described in the above patent document, movements of the first and second insulators in the direction in which the sensor element is resiliently held are not restricted. Accordingly, the sensor element may move in the direction in which the sensor element is resiliently held by the electrode spring at the time of assembling the gas sensor, for example.

Therefore, it may occur that electrical continuity between the sensor element and the electrode spring becomes insufficient due to sensor-to-sensor variation in the spring load applied to the sensor element. Meanwhile, there is a strong demand to make such a gas sensor compact in size for the purpose of improving its performance (early activation, for example) and reducing its manufacturing cost. As the size of the gas sensor becomes smaller, the required assembly accuracy becomes higher, and accordingly the above problem becomes more pronounced.

SUMMARY

An exemplary embodiment provides a gas sensor including:

a sensor element for detecting a concentration of a specific gas contained in a measurement gas;

a first insulator inside which the sensor element is inserted and held;

a second insulator disposed on a proximal side of the first insulator so as to cover a proximal side of the sensor element; and a contact member held by the second insulator and sandwiching the sensor element in a state of being in contact with an electrode terminal of the sensor element, wherein a proximal end portion of the first insulator and a distal end portion of the second insulator abut on each other in an axial direction of the gas sensor, and each of the proximal end portion of the first insulator and the distal end portion of the second insulator is provided with a positioning structure, the positioning structure being configured to restrict a relative movement between the first and second insulators in a sandwiching direction in which the sensor element is sandwiched by the contact member and in an orthogonal direction perpendicular to the sandwiching direction and in the axial direction.

According to the exemplary embodiment, there is provided a gas sensor which is high in assembly accuracy, and can prevent reduction of the spring load of its contact member and a resultant defective electrical continuity.

Other advantages and features of the invention will become apparent from the following description including the drawings and claims.

PREFERRED EMBODIMENTS OF THE INVENTION

In the below-described embodiments, the term "distal side" refers to the side of a gas sensor at which the gas sensor is exposed to a measurement gas, and the term "proximity side" refers to the side of the gas sensor opposite to the distal side.

First Embodiment

A gas sensor 1 according to an embodiment of the invention is with reference to FIGS. 1 to 7. As shown in FIGS. 1 to 7, the gas sensor 1 according to this embodiment includes a sensor element 2 for detecting a concentration of a specific gas contained in a measurement gas, a first insulator 3 through which the sensor element 2 is inserted to be held therein, a second insulator 4 disposed on the proximal side of the first insulator 3 so as to cover the proximal side of the sensor element 2 and contact members 5 held by the second insulator 4 so as to be in contact with electrode terminals 221 of the sensor element 2 to resiliently hold the sensor element 2.

The proximal end portion 32 of the first insulator 3 and the distal end portion 41 of the second insulator second insulator 4 abut against each other in the axial direction X of the gas sensor. A positioning structure 10 is provided in each of the proximal end portion 32 of the first insulator and the distal end portion 41 of the second insulator 4. The positioning structure 10 is configured to restrict a relative movement between the first insulator 3 and the second insulator 4 in the sandwiching direction Y in which the sensor element 2 is sandwiched by the contact members 5 and in the orthogonal direction Z perpendicular to the sandwiching direction Y and the axial direction X.

Figure 1:
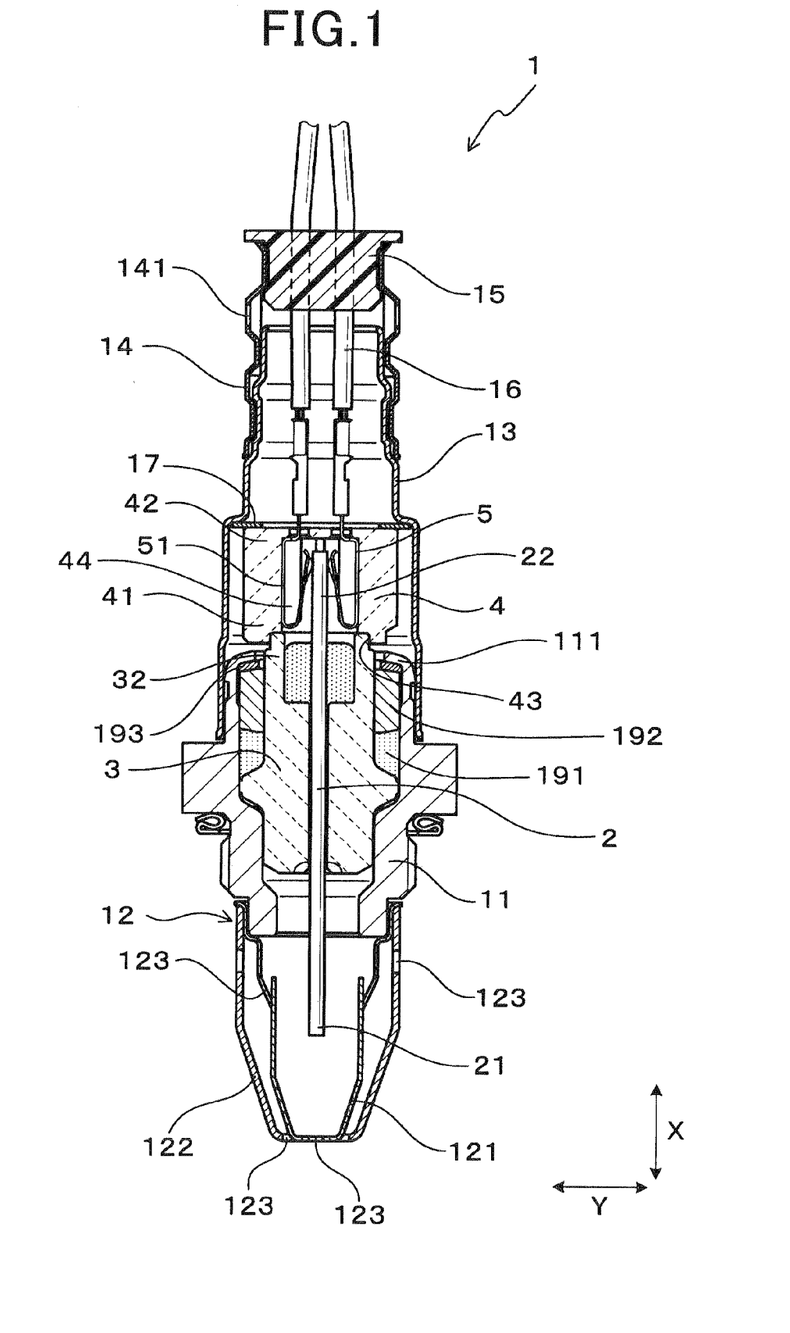
FIG. 1 is a cross-sectional view of a gas sensor according to an embodiment of the invention.

As shown in FIG. 1, the sensor element 2 is inserted and held inside the first insulator 3. The first insulator 3 is held inside a housing 11.

Figure 2:
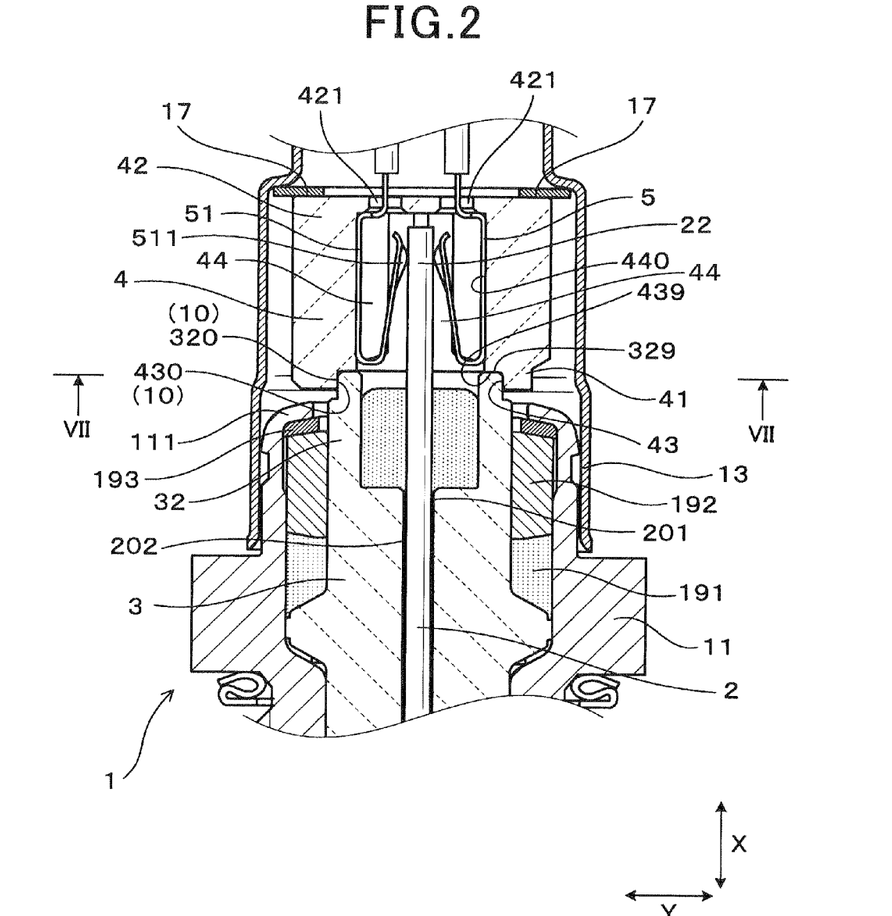
FIG. 2 is a partial cross-sectional view of the gas sensor showing its first and second insulator and their vicinities.

As shown in FIG. 2, a sealing member 191 made of filling material is disposed between the first insulator 3 and the housing 11. An insulating member 192 made of insulating material is disposed on the proximal side of the sealing member 191. A metal ring member 193 having an approximately planar shape is disposed on the proximal side of the insulating member 192. The sealing member 191, the insulating member 192 and the metal ring member 193 are swaged and fixed in a state of being pressed in the direction from the proximal side to the distal side by a swage cover portion 111 formed by bending the proximal end portion of the housing 11 inwardly, so that the space between the first insulator 3 and the housing 11 is hermeticaly sealed. In this embodiment, the filling material of the sealing member 191 is talc.

As shown in FIG. 1, on the distal side of the housing 11, there is provided a double-structured distal-side cover 12 constituted of an inner cover 121 covering the distal end portion 21 of the sensor element 2 and an outer cover 122 disposed outside the inner cover 121. Each of the inner cover 121 and the outer cover 122 is formed with air holes 123 for introducing and discharging the measurement gas.

A first proximal-side cover 13 is fixed to the proximal side of the housing 11 so as to cover the proximal end portion 22 of the sensor element 2. A second proximal-side cover 14 is fixed to the proximal side of the first proximal-side cover 13. The second proximal-side cover 14 is formed with air holes 141 for introducing air. The second proximal-side cover 14 is formed with an opening at its proximal side, which is closed by a sealing member 15 such as a rubber bushing. Four lead members 16 are disposed so as to penetrate through the sealing member 15 to be connected externally.

Figure 5:
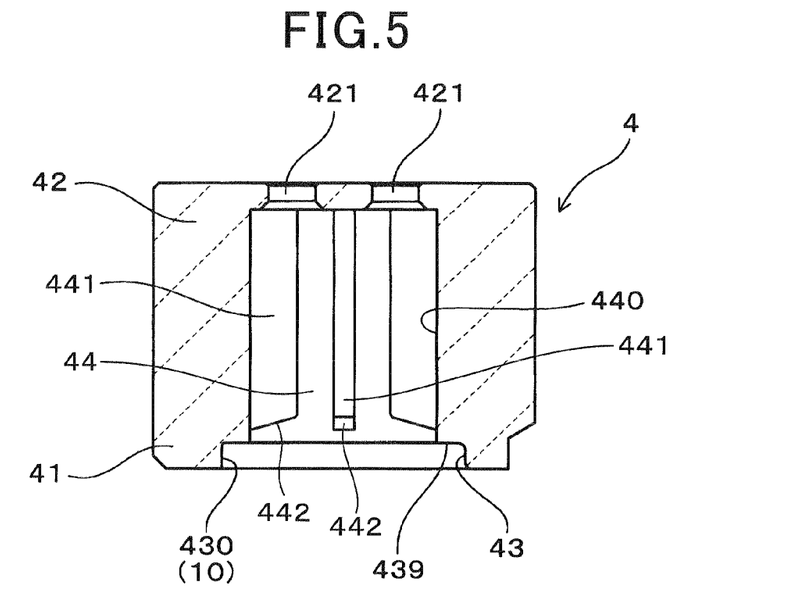
FIG. 5 is a cross-sectional view showing the structure of the second insulator.

As shown in FIGS. 2 and 5, the second insulator 4 covering the proximal end portion 22 of the sensor element 2 is disposed on the proximal side of the first insulator 3 within the first proximal-side cover 13. The second insulator 4 is formed with an inner space 44 for accommodating therein the proximal end portion 22 of the sensor element 2. The proximal end portion 42 of the second insulator 4 is formed with four insertion holes 421 through which the contact members 5 penetrate, respectively. The insertion holes 421 are in communication with the inner space 44 in the axial direction X.

As shown in FIG. 2, the contact members 5 are held inside the inner space 44 of the second insulator 4. The contact members 5 are constituted of four spring terminals 51 formed by bending a metal plate. Each of the spring terminals 51 is connected to a corresponding one of leads 16. Each of the spring terminals 51 is inserted through a corresponding one of the insertion holes 421 formed in the second insulator 4, and supported by the inner wall surface 440 of the inner space 44. Each of the spring terminals 51 is accommodated within the inner space 44 in a state of being bent inward. Each of the spring terminals 51 includes a contact portion 511 formed in its portion bent inward, which is in contact with a corresponding one of the electrode terminals 221.

Figure 6:
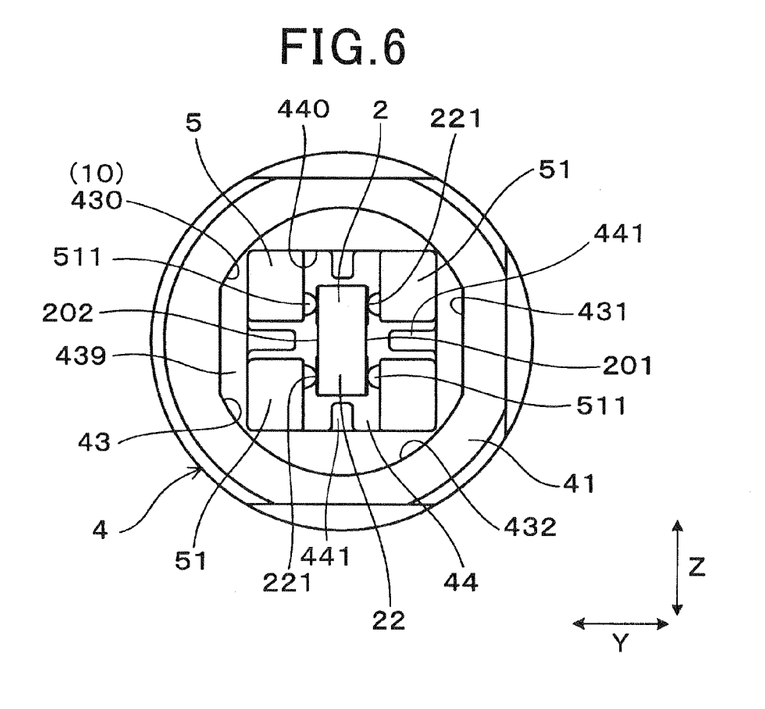
FIG. 6 is a diagram showing a sensor element included in the gas sensor as viewed from the axially distal side of the second insulator in a state where the sensor element is held by a contact member.

As shown in FIG. 6, the inner wall surface 440 is formed with four separating portions 441 (see FIGS. 4 and 5) for preventing the spring terminals 51 from contacting with one another within the inner space 44. As shown in FIG. 5, the second insulator 4 is formed with a distal concave portion 43 at its distal end. The distal end surfaces 442 of the separating portions 441 are located closer to the proximal side than the bottom surface 439 of the distal concave portion 43 is so that the distal end portions 442 of the separating portions 441 are not located flush with the bottom surface 439 of the distal concave portion 43. As a result, since increase of the molding density during pressure molding at the corners between the inner wall surface 440 and the surfaces of the separating portions 441 can be prevented from occurring near the bottom surface 439 of the distal concave portion 43, surface undulation of the bottom surface 439 after a firing process can be suppressed. Hence, as described later, it becomes possible to prevent occurrence of breakage or cracks in the bottom surface 439 due to stress concentration in the bottom surface 439 when the abutment surface 329 of the first insulator 3 abuts on the bottom surface 439 of the distal concave portion 43 of the second insulator 4. Preferably, the distance between the distal end surface 442 of the separating portions 441 and the bottom surface 439 of the distal concave portion 43 is between 0.4 mm and 0.8 mm.

As shown in FIG. 6, each of the principal surfaces 201 and 202 of the proximal end portion 22 of the sensor element 2 is provided with a pair of the electrode terminals 221. Two of the spring terminals 51 are disposed to be in contact with a principal surface 201 of the sensor element 2, and the other two of the spring terminals 51 are disposed to be in contact with the other principal surface 202 of the sensor element 2. Each of the spring terminals 51 includes a terminal portion which contacts with a corresponding one of the electrode terminals 221 of the sensor element 2. Accordingly, the sensor element 2 is sandwiched by the four spring terminals at its both principal surfaces 201 and 202. In this embodiment, the width of the sensor element 2 in the orthogonal direction Z perpendicular to the sandwiching direction Y is 3.9 mm.

Figure 3A:
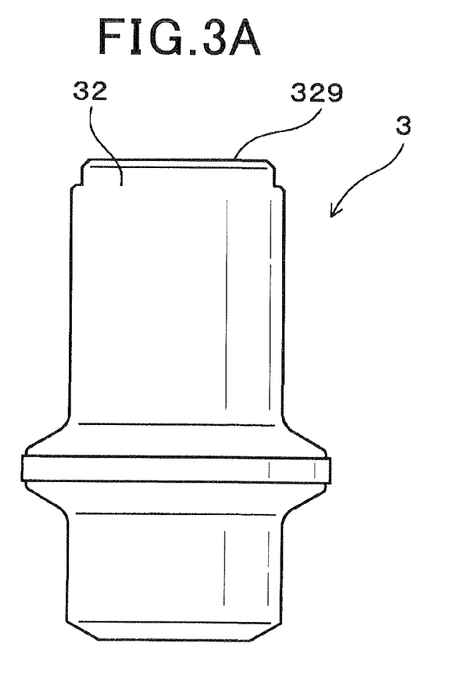
FIG. 3A is a front view of the first insulator.
Figure 3B:
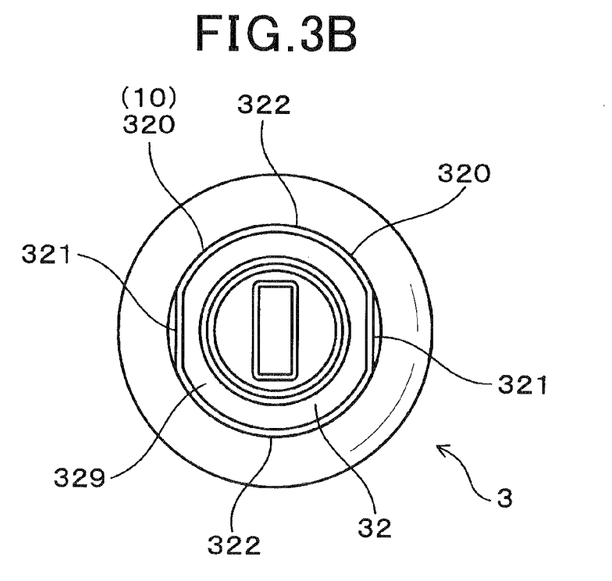
FIG. 3B is a diagram showing the first insulator as viewed from the axially proximal side thereof.

As shown in FIG. 2, the proximal end portion 32 of the first insulator 3 is formed in a cylindrical shape. As shown in FIGS. 3A and 3B, the proximal end portion 32 of the first insulator 3 is formed with the abutment surface 329 which abuts on the distal end portion 41 of the second insulator 4.

Figure 4A:
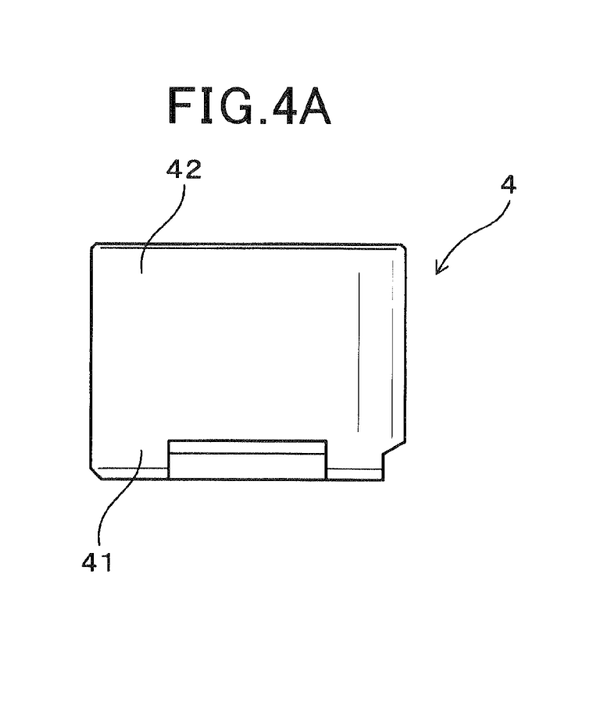
FIG. 4A is a front view of the second insulator.
Figure 4B:
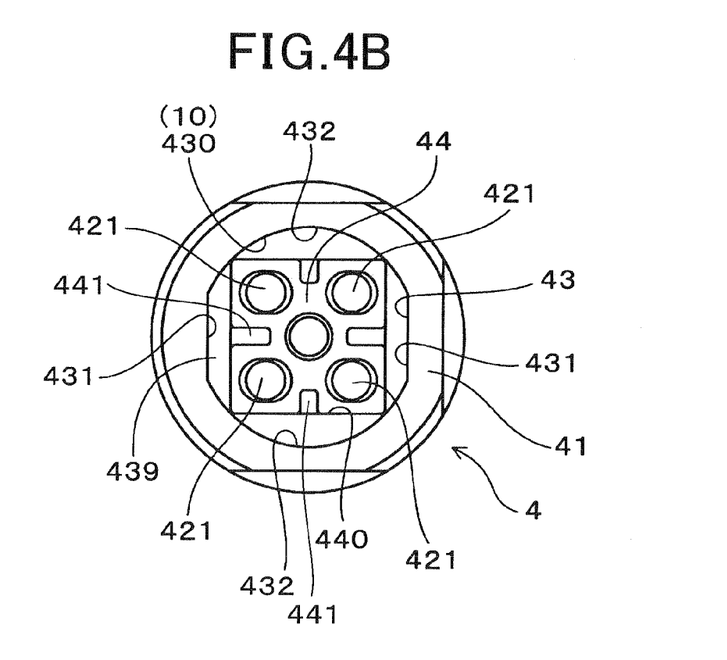
FIG. 4B is a diagram showing the second insulator as viewed from the axially distal side thereof.

As shown in FIGS. 4A and 4B, the distal end portion 41 of the second insulator 4 is formed with the distal concave portion 43 dented toward the proximal side. As shown in FIG. 5, the distal concave portion 43 is in communication with the inner space 44 along the axial direction X. The inner diameter of the distal concave portion 43 is larger than the outer diameter of the proximal end portion 32 of the first insulator 3.

As shown in FIG. 2, the proximal end portion 32 of the first insulator 3 and the distal end portion 41 of the second insulator 4 abut on each other in the axial direction X. More specifically, the abutment surface 329 of the first insulator 3 abuts on the bottom surface 439 of the distal concave portion 43 of the second insulator 4. The proximal end portion 32 of the first insulator 3 is accommodated in the distal concave portion 43 of the second insulator 4. The distal concave portion 43 of the second insulator 4 covers the entire circumference of the proximal end portion 32 of the first insulator 3.

Figure 7:
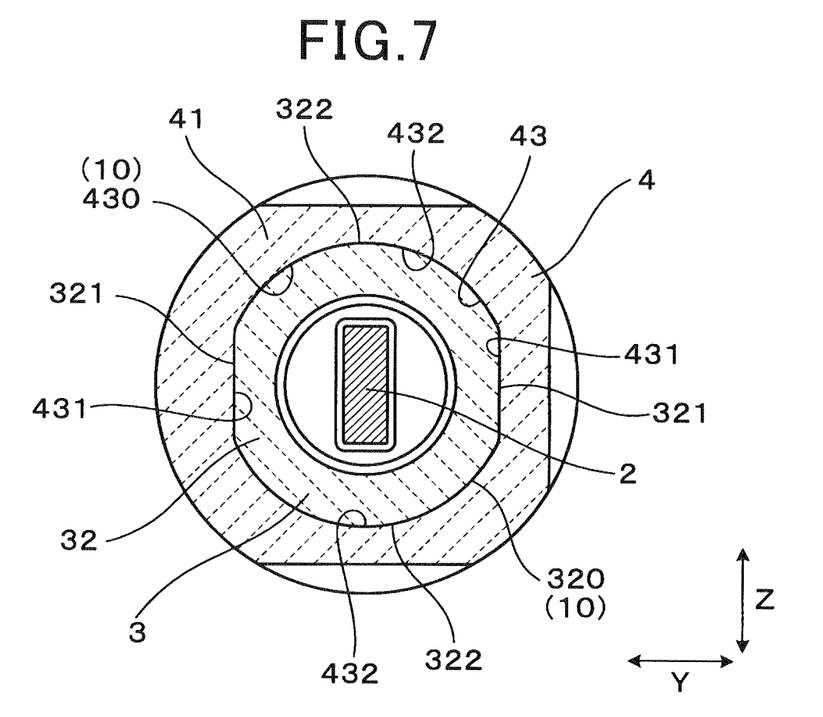
FIG. 7 is a cross-sectional view of FIG. 2 taken along line VII-VII.

As shown in FIG. 7, each of the proximal end portion 32 of the first insulator 3 and the distal end portion 41 of the second insulator 4 is formed with the positioning structure 10. The positioning structure 10 is constituted of the outer peripheral surface 320 of the proximal end portion 32 of the first insulator 3 and the inner peripheral surface 430 of the distal concave portion 43 of the second insulator 4. The positioning structure 10 is configured to restrict a relative movement in each of the sandwiching direction Y and the orthogonal direction Z perpendicular to the sandwiching direction Y between the first insulator 3 and the second insulator 4.

More specifically, the inner peripheral surface 430 of the distal concave portion 43 of the second insulator 4 includes a pair of planar surface portions 431 parallel to each other and radially opposite to each other and a pair of convex curved surface portions 432 connecting between the pair of planar surface portions 431. The planar surface portion 431 is formed so as to extend linearly in the orthogonal direction Z perpendicular to the sandwiching direction Y, and have its cross section perpendicular to the axial direction X. The curved surface portion 432 is formed to have a convex circular-arc shape in its cross section perpendicular to the axial direction X.

The outer peripheral surface 320 of the proximal end portion 32 of the first insulator 3 has a shape complementary to that of the inner peripheral surface 430 of the distal concave portion 43 of the second insulator 4. That is, the outer peripheral surface 320 includes a pair of planar surface portions 321 facing the pair of the planar surface portions 431 of the second insulator 4, and a pair of curved surface portions 322 connecting between the pair of planar surface portions 321. The planar surface portion 321 is formed so as to extend linearly in the orthogonal direction Z perpendicular to the sandwiching direction Y, and have its cross section perpendicular to the axial direction X. The curved surface portion 322 is formed to have a concave circular-arc shape in its cross section perpendicular to the axial direction X.

Since the outer peripheral surface 320 of the proximal end portion 32 of the first insulator 3 and the inner peripheral surface 430 of the distal concave portion 43 of the second insulator 4 fit each other, movements of the first and second insulators 3 and 4 in the sandwiching direction Y and the orthogonal direction Z are restricted. More precisely, since the planar surface portions 321 and the curved surface portions 322 of the outer peripheral surface 320 of the proximal end portion 32 of the first insulator 3 respectively fit the planar surface portions 431 and the curved surface portions 432 of the inner peripheral surface 430 of the distal concave portion 43 of the second insulator 4, movements of the first and second insulators 3 and 4 in the sandwiching direction Y and the orthogonal direction Z are restricted.

Further, since the outer peripheral surface 320 of the proximal end portion 32 of the first insulator 3 and the inner peripheral surface 430 of the distal concave portion 43 of the second insulator 4 are formed so as to face and mate with each other at their planar surface portions 321 and 431, the first and second insulators 3 and 4 do not rotate in the circumferential direction relative to each other. That is, relative movement in the circumferential direction between the first and second insulators 3 and 4 are restricted.

As shown in FIG. 2, a disc spring 17 having an annular shape is disposed between the proximal end portion 42 of the second insulator 4 and the first proximal-side cover 13. The second insulator 4 is held in a state of being pressed toward the distal side, that is, toward the side of the first insulator 3 by the disc spring 17. Accordingly, movements in the axial direction X of the first and second insulators 3 and 4 are restricted. The load of the disc spring 17 may be set as low as between 0.4 and 1.0 kN so that movement of the second insulator 4 relative to the first insulator 3 is sufficiently restricted, and also cracks do not occur in the second insulator 4.

The gas sensor 1 described above provides the following advantages. The proximal end portion 32 of the first insulator 3 and the distal end portion 41 of the second insulator 4 abut on each other in the axial direction X. Each of the proximal end portion 32 of the first insulator 3 and the distal end portion 41 of the second insulator 4 is provided with the positioning structure 10. The positioning structure 10 is configured to restrict relative movement in the sandwiching direction Y and the orthogonal direction Z perpendicular to the sandwiching direction Y between the first insulator 3 and the second insulator 4.

Since the first and second insulators 3 and 4 are restricted from moving relative to each other in the sandwiching direction Y, the sensor element 2 held by the first insulator 3 can be positioned accurately by the contact members 5 held by the second insulator 4. Accordingly, since variations of the loads applied to both sides of the sensor element 2 in the sandwiching direction Y by the contact members 5 are small, defective electrical continuity due to reduction of the spring load at one of both sides of the sensor element 2 can be prevented.

Further, the first and second insulators 3 and 4 are restricted from moving relative to each other also in the orthogonal direction perpendicular to the sandwiching direction Y. Accordingly, the electrode terminals 221 of the sensor element 2 held by the first insulator 3 can be accurately reliably contacted with the contact members 5 held by the second insulator 4 during assembly. As a result, positional deviation in the orthogonal direction Z between the electrode terminals 221 of the sensor element 2 and the contact members 5 can be suppressed to thereby prevent deviation of the contact members 5 and a resultant defective electrical continuity.

Further, since the positioning structure 10 restricts relative movement in the sandwiching direction Y and the orthogonal direction Z perpendicular to the sandwiching direction Y between the first insulator 3 and the second insulator 4 as described above, it is possible to assemble the first and second insulators 3 and 4 in place with a high degree of accuracy. Accordingly, the gas sensor 1 can be made sufficiently small in size without impairing assembly accuracy.

The distal end portion 41 of the second insulator 4 is formed with the distal concave portion 43 which is dented toward the proximal side, and covers the entire circumference of the proximal end portion 32 of the first insulator 3. The positioning structure is constituted of the outer peripheral surface 320 of the proximal end portion 32 of the first insulator 3 and the inner peripheral surface 430 of the distal concave portion 43 of the second insulator 4, which are fittable to each other. Accordingly, movements in the sandwiching direction Y and the orthogonal direction Z of the first and the second insulators 3 and 4 can be restricted further reliably, and assembly of the first and second insulators 3 and 4 can be further facilitated.

The proximal end portion 32 of the first insulator 3 is formed with the abutment surface 329 for abutment with the distal end portion 41 of the second insulator 4. The abutment surface 329 abuts on the bottom surface 439 of the distal concave portion 43 of the second insulator 4. Accordingly, the first and second insulators 3 and 4 can be positioned in place in the axial direction X accurately and easily.

The outer peripheral surface 320 of the proximal end portion 32 of the first insulator 3 and the inner peripheral surface 430 of the distal concave portion 43 of the second insulator 4 include the planar surface portions 321 and 431, respectively, which are opposite to each other. Accordingly, the first and second insulators 3 and 4 can be prevented from rotating in the circumferential direction relative to each other. That is, the first and second insulators 3 and 4 can be prevented from moving circumferentially by the provision of the planar surface portions 321 and 431. Also, the provision of the planar surface portions 321 and 431 facilitates assembling between the first and second insulator 3 and 4.

The inner peripheral surface 430 of the distal concave portion 43 of the second insulator 4 includes the pair of the planar surface portions 431 radially opposite to each other, while on the other hand, the outer peripheral surface 320 of the proximal end portion 32 of the first insulator 3 includes the pair of the planar surface portions 321 mating with the pair of planar surface portions 431. Accordingly, the first and second insulators 3 and 4 can be further reliably restricted from moving circumferentially, and assembling between the first and second insulator 3 and 4 can be further facilitated.

The first and second insulators 3 and 4 are pressed and held in a state of abutting on each other in the axial direction by the disc spring 17. Accordingly, the first and second insulators 3 and 4 can be restricted from moving in the axial direction X. This makes it possible to further increase the accuracy of positioning of the first and second insulators 3 and 4.

As explained above, according to the embodiment described above, there is provided the gas sensor 1 which is excellent in assembling accuracy, and resistant to deviation of the contact members 5 and to a resultant defective electrical continuity.

In the above embodiment, the positioning structure 10 is constituted of the outer peripheral surface 320 of the proximal end portion 32 of the first insulator 3 and the inner peripheral surface 430 of the distal concave portion 43 of the second insulator 4, which mate with each other. However, to further reliably restrict movements of the first and second insulators 3 and 4 in the sandwiching direction Y, the orthogonal direction Z and the circumferential direction, each of the outer peripheral surface 320 of the proximal end portion 32 of the first insulator 3 and the inner peripheral surface 430 of the distant concave portion 43 of the second insulator 4 may be formed with a projection and a recess which are complementary to each other.

The above explained preferred embodiments are exemplary of the invention of the present application which is described solely by the claims appended below. It should be understood that modifications of the preferred embodiments may be made as would occur to one of skill in the art.

In the above embodiment, the number of pieces of each of the lead members 16 and the contact members 5 is four. However, the present invention is applicable to a case where the number of them is other than four. That is, they may be less than four, or five or more in number.

What is claimed is:

1. A gas sensor comprising:
   a sensor element for detecting a concentration of a specific gas contained in a measurement gas;
   a first insulator inside which the sensor element is inserted and held;
   a second insulator disposed on a proximal side of the first insulator so as to cover a proximal side of the sensor element; and
   at least one contact member held by the second insulator and sandwiching the sensor element in a state of being in contact with an electrode terminal of the sensor element,
   wherein
   a proximal end portion of the first insulator and a distal end portion of the second insulator abut on each other in an axial direction of the gas sensor,
   each of the proximal end portion of the first insulator and the distal end portion of the second insulator is provided with a positioning structure,
   the distal end portion of the second insulator is formed with a distal end concave portion dented toward a proximal side thereof and covering an entire circumference of the proximal end portion of the first insulator, and the positioning structure comprises a projection including a perimeter that is part of an outer peripheral surface of the proximal end portion of the first insulator and comprises an inner peripheral surface of the distal concave portion of the second insulator,
   the inner peripheral surface of the distal concave portion of the second insulator and the outer peripheral surface of the proximal end portion of the first insulator are fitted to each other so that the inner peripheral surface completely surrounds the perimeter,
   the positioning structure is configured to restrict a relative movement between the first and second insulators in a sandwiching direction in which the sensor element is sandwiched by the contact member and in an orthogonal direction perpendicular to the sandwiching direction and in the axial direction by fitting the inner peripheral surface of the distal concave portion of the second insulator to the outer peripheral surface of the proximal end portion of the first insulator, and
   the proximal end portion of the first insulator is formed with an abutment surface for abutment with the distal end portion of the second insulator, the abutment surface abutting directly on a bottom surface of the distal concave portion of the second insulator.

2. The gas sensor according to claim 1, wherein the contact member is four or more in number.

3. The gas sensor according to claim 1, wherein the distal end concave portion covering the entire circumference of the proximal end portion of the first insulator restricts the relative movement between the first and second insulators in the sandwiching direction and in the orthogonal direction perpendicular to the sandwiching direction.

4. The gas sensor according to claim 1, further comprising an intermediate member disposed between a cover and the second insulator, the second insulator being pressed by the intermediate member.

5. The gas sensor according to claim 1, wherein the outer peripheral surface of the proximal end portion of the first insulator includes at least one first planar surface portion at the perimeter, and the inner surface of the distal concave portion of the second insulator includes at least one second planar surface portion mating with the first planar surface portion.

6. The gas sensor according to claim 5, wherein the inner peripheral surface of the distal concave portion of the second insulator includes a pair of the second planar surface portions parallel to each other and radially opposite to each other, and the outer peripheral surface of the proximal end portion of the first insulator includes, at the perimeter, a pair of the first planar surface portions each mating with a corresponding one of the pair of the second planar surface portions.

\* \* \* \* \*